United States Patent [19]

Dewhirst et al.

[11] Patent Number: 4,847,011
[45] Date of Patent: Jul. 11, 1989

[54] BIS-ANTHROLS AND BIS-NAPHTHOLS AND DIGLYCIDYL ETHERS THEREOF

[75] Inventors: Kenneth C. Dewhirst; Thomas G. Stewart, Jr., both of Houston, Tex.

[73] Assignee: Shell Oil Company, Houston, Tex.

[21] Appl. No.: 107,618

[22] Filed: Oct. 9, 1987

[51] Int. Cl.[4] .................. C07C 39/12; C07C 50/16; C09B 1/00; C09B 3/00

[52] U.S. Cl. .................. 260/351; 568/719; 568/721

[58] Field of Search .............. 260/351; 568/719

[56] References Cited

U.S. PATENT DOCUMENTS

| | | | |
|---|---|---|---|
| 1,841,342 | 1/1932 | Teppema | 568/719 |
| 2,057,676 | 10/1936 | Graves | 568/719 |
| 2,480,533 | 8/1949 | Winnek | 568/719 |
| 2,791,616 | 5/1957 | Luten | 568/719 |
| 2,819,974 | 1/1958 | Bell et al. | 568/719 |
| 4,205,005 | 5/1980 | Fahey | 260/351 |
| 4,551,508 | 11/1985 | Urasaki | 528/88 |

FOREIGN PATENT DOCUMENTS

| | | | |
|---|---|---|---|
| 299972 | 11/1928 | United Kingdom | 260/351 |
| 874869 | 8/1961 | United Kingdom | 568/719 |
| 935061 | 8/1963 | United Kingdom | 568/719 |

OTHER PUBLICATIONS

61 CA 3047, (1964).
"Beilstein", 6, 1053, E2, 1028.
Morgan, P. W., *Macromolecules*, 3, 536–544, (1970).
Chen, C. S. et al., *J. Applied Polymer Science*, 27, 3292, (1982).
Jedlinski et al., *Przemyslu Chem.*, 46(5), 272–274, (1967).

*Primary Examiner*—John Kight
*Assistant Examiner*—Frederick Krass

[57] ABSTRACT

Certain bis-anthrols and bis-naphthols and their diglycidyl ethers are novel and useful in the preparation of new polyether thermoplastic compositions. The compounds have the formulae:

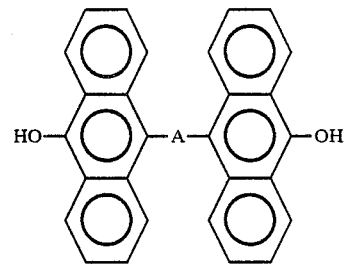

I.

(or its keto tautomer) or

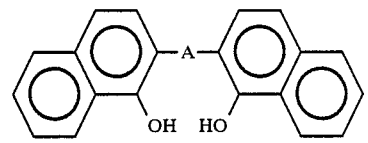

II.

where A is as defined in the claims.

7 Claims, No Drawings

BIS-ANTHROLS AND BIS-NAPHTHOLS AND DIGLYCIDYL ETHERS THEREOF

FIELD OF THE INVENTION

The present invention relates to new bis-anthrols and bis-naphthols and to glycidyl ethers thereof.

BACKGROUND OF THE INVENTION

A variety of bis-phenols are known in the art which are used to prepare polyethers by reaction with epichlorohydrin. For example, U.S. Pat. No. 3,410,825 describes certain bis[p-(2,3-epoxypropoxy) phenyl] polycyclic hydrocarbons and polyethers thereof. The resulting polyethers are useful in such applications as molding, extrusion, adhesives, coatings and the like. However, the various polyethers must be highly crosslinked to improve their high temperature properties for certain uses, such as by the aerospace industry, but such high crosslinking results in generally lower toughness. What is needed is a resin system that combines the good property advantages of excellent high temperature properties along with high toughness and also good processability (extrusion) by a thermosetting resin technique.

Certain bis-anthrols and bis-naphthols are known in the art as in Jedlinski et al., *Przemyslu Chem.*, 46(5), 272-274 (1967); Beilstein, 6, 1053; E2, 1028; Morgan, *Macromolecules*, 3, 536 (1970) and Chen, *Journal of Applied Polymer Science*, 27, 3292 (1982). Such materials have found little, if any, use in the polymer art and not for polyethers having useful properties, e.g., the aerospace industry. Accordingly, there is a need for new resins which could be prepared from new monomers which would provide structural components to give new properties to polyether resins.

SUMMARY OF THE INVENTION

The present invention is directed to new bis-anthrols and bis-naphthols of the formulas Ia and Ib or the keto tautomer of Ia

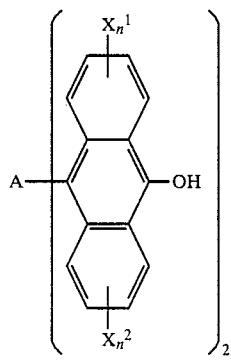

Ia

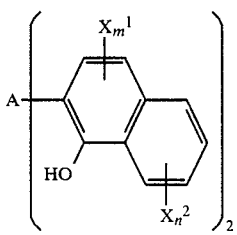

Ib wherein $X^1$ and $X^2$ each independently is an alkyl group containing 1 to 4 carbon atoms or a halogen atom having an atomic number of from 9 to 35, inclusive; m is 0, 1 or 2; n is 0, 1, 2, 3 or 4; and A is a divalent hydrocarbon radical selected from the group consisting of an alylene group containing from 3 to 8 carbon atoms, or a radical derived from a non-aromatic carbocyclic group or a dialkyl aromatic or non-aromatic carbocyclic group containing from 7 to 24 carbon atoms in which each alkyl group contains from 1 to 8 carbon atoms and the carbocyclic group comprises a central non-aromatic ring containing 5 to 7 carbon atoms in a ring or a central aromatic carbocyclic ring, each central ring optionally bridged or fused with a non-aromatic or aromatic carbocyclic ring. When A is a dialkyl aromatic or non-aromatic carbocyclic group it should be understood that the bonds from A to the anthrol or naphthol group are from the alkyl substituents of the dialkyl carbocyclic group.

In the compounds of Formulas Ia and Ib, $X^1$ and $X^2$ each independently is an alkyl group containing from 1-4 carbon atoms such as methyl, ethyl or the like or a halogen atom having an atomic number of from 9 to 35 such as chlorine or fluorine. Preferably, when $X^1$ or $X^2$ is present, each is a methyl group or a chlorine atom. m is 0, 1 or 2 and preferably 0 or 1; n is 0, 1, 2, 3 or 4 and preferably each of m and n independently is 0 or 1. In one embodiments, m and n are both 0.

A is a group selected from an alkylene group containing from 3 to 8 carbon atoms; or a non-aromatic carbocyclic group or a dialkyl aromatic or non-aromatic group containing from 7 to 24 carbon atoms and a central non-aromatic ring containing 5 to 7 carbon atoms in a ring or a central aromatic carbocyclic ring, each central ring optionally bridged or fused on each side with a non-aromatic or aromatic carbocyclic ring. In one preferred embodiment, A is derived from a dialkylaromatic carbocyclic group containing 12 to 20 carbon atoms in which each alkyl group contains from 3 to 5 carbon atoms, and the anthrol or naphthol is attached to the alkyl substituent of the dialkylaromatic carbocyclic group. The alkylene, carbocyclic and dialkylcarbocyclic groups include 2,2-isopropylidene, anthrylene, fluorenylene, phenylene-diisopropylidene, norcamphanylidene, adamantylene, naphthylene, and equivalent kinds of groups. Preferably, A is naphthylene-diisopropylidene or phenylenediisopropylidene.

Bis-naphthols are preferred because they are easier to use as monomers and diglycidyl ethers and the resulting polyethers are also easier to handle and have very desirable mechanical properties.

The bis-anthrols of Formula Ia and the bis-naphthols of Formula Ib are prepared by alkylating the appropriately $X_m^1$ and $X_n^2$ substituted or unsubstituted 9-anthrols or 1-naphthol with conventional bis or higher functionality alkylating agents. Suitable alkylating agents include olefins, alcohols, halogenated hydrocarbons, carbonyl compounds and the like. For example, the alkylating agent is p-diisopropenylbenzene, bis-p-(1-hydroxy-1-methylethyl) benzene, bis-p-(1-chloro-1-methylethyl) benzene and the like. Bis-anthrols are also prepared by alkylating the corresponding 9-anthrone via its 9-hydroxy intermediate, particularly with a bis-alcohol alkylating agent.

The alkylations are conducted by conventional procedures known in the art for the alkylation of aromatic alcohols or carbonyl compounds. For example, the 9-anthrols or 1-naphthols are treated with the appropriate bis-tertiary alcohol compound, e.g., bis-p-(1- hydroxy-1-methylethyl)benzene, in the presence of 1,1,1-trichloro-ethane, p-toluenesulfonic acid or hydrochloric acid and the like and optionally 3-mercaptopropionic acid at reflux. In the case of the 1-naphthol, the alkylation occurs unexpectedly almost exclusively at the position ortho to the phenolic hydroxyl group.

The present invention is also directed to a diglycidyl ether of a bis-anthrol or a bis-naphthol of the Formula IIa and IIb or of the keto tautomer of Ia.

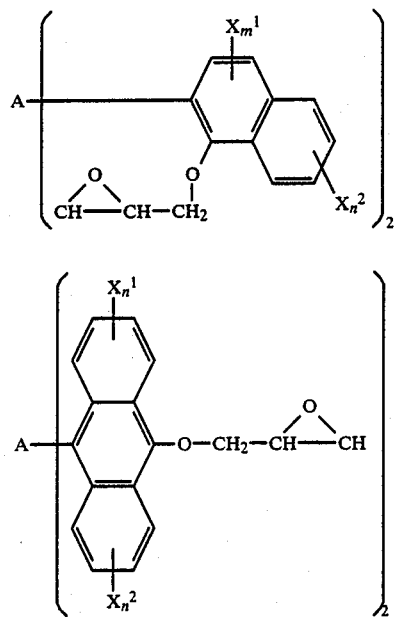

wherein A has the same meaning and preferences as set forth in Formulas Ia and Ib above.

The diglycidyl ethers of the bis-anthrols or bis-naphthols of Formula Ia or Ib can be prepared by treating a bis-anthrol or a bis-naphthol with epichlorohydrin or epibromohydrin in the presence of a strong base such as sodium hydroxide or the like as is conventionally known in the art for the glycidylation of phenols. The reaction is usually conducted under relatively mild conditions of temperature and pressure. For example, the reaction can be conducted at from about 20° C. to about 120° C. at normal pressure. Depending on the solubility of the bis-anthrol or bis-naphthol, the reaction is conducted in the absence or presence of conventional alcohol, ether, ester or aromatic or aliphatic hydrocarbon solvents and the like. For example, the reaction is conducted at about 50° C. to 90° C. in a solvent such as diethyl ether, toluene, xylene, ethyl acetate, ethyl isobutyrate, ethanol or, especially, isopropanol.

In the case of bis-anthrols, the keto tautomer tends to be the primary product unless the reaction is controlled in favor of the bis-phenol tautomer, e.g., by generating bis-phenate ion prior to adding the epihalohydrin using potassium tertiary-butoxide in slight excess of the bis-anthrol.

The bis-naphthols and their diglycidyl ethers are purified and recovered by conventional techniques of solvent extraction and the like. The bis-anthrols and their digylcidyl ethers are somewhat difficult to purify by solvent extraction and may require the use of conventional chromatographic techniques if highly pure materials are required.

The diglycidyl ethers of bis-anthrol or bis-naphthol having the Formula IIa or IIb are useful to prepare various conventional kinds of polymers, such as polyether amines and polyethers, including high melting, high molecular weight polyethers, composed essentially of recurring linear units of Formula III.

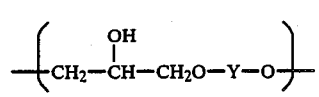

which are homopolymers or are copolymers wherein at least a minor amount, e.g., 10 mole percent, of Y is the group remaining after removal of the terminal hydroxy groups from bis-anthrol or bis-naphthol of Formula Ia or Ib above wherein A, $X^1$, $X^2$, m and n have the meanings previously shown and a major amount, e.g., not more than 90 mole percent, of Y is the group remaining after removal of the terminal hydroxy groups from a different bis-phenol compound including a different bis-anthrol, bis-naphthol or a conventional bis-phenol including those illustrated herein after.

The curable linear molecules of polyether or polyether amine compositions are prepared by (1) reacting a bis-anthrol or bis-naphthol of Formula Ia or Ib above with a different conventional bis-phenol component or diglycidyl ether thereof and optionally a multifunctional phenol or amine in the presence of base or (2) alternatively reacting a diglycidyl ether of a bis-anthrol or bis-naphthol alone or (a) also with a conventional bis-phenol in the presence of base or (b) with a di-secondary amine component alone and optionally a multifunctional phenol or amine. These molecules can be with or without light crosslinking.

A preferred use of the compounds of Formulas Ia or Ib and IIa or IIb of the invention is to make (co)-polyether thermoplastic compositions having flexible portions and bulky stiff portions, prepared by reacting a diepoxide of a bis-hydroxy compound with a bis-phenol compound or an amine to form linear molecules and lightly cross-linking the resulting linear molecule. Such polyether and polyether amine thermoplastic compositions are broadly but not specifically disclosed in co-pending U.S. patent application Ser. Nos. 871,950 with amines, 871,951 and 871,952, all filed June 9, 1986, the disclosures of which are incorporated by reference and representatively illustrated in detail below in which the flexible portions and bulky stiff portions can be derived from the bis-anthrols or bis-naphthols or diglycidyl ethers thereof, which compounds comprise the present invention.

The compounds of the invention can be used in polyether thermoplastic compositions including, for example, those linear molecules having the repeating structure

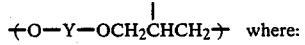

where:

(a) "X" and "Y" represent a segment comprising stiff units (SU) and optional flexible units (FU), which stiff units and flexible units are interconnected;

(b) said stiff units, SU and SU', are independently selected from the group consisting of substituted and non-substituted aromatic rings, cycloaliphatic rings and heterocyclic rings;

(c) said flexible units which permit rotation at an angle, FU and FU', are independently selected from the group consisting of

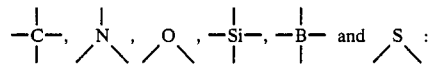

(d) the number of "X" segments in said molecules are "a", the number of "Y" segments in said molecules are "b", and the ratio of $$\frac{a}{a+b}$$

is between zero and one;

(e) the ratio of the number of stiff units to flexible units in said "X" segment (SU/FU) is equal to or greater than the ratio of the number of stiff units to flexible units in said flexible "Y" segment (SU'/FU');

(f) the number of stiff units and flexible units are selected such that the average number of total stiff units $$\left(\left(\frac{a}{a+b}\right) \cdot SU\right) + \left(\left(\frac{b}{a+b}\right) \cdot SU'\right)$$

divided by the average number of total flexible units $$\left(\left(\frac{a}{a+b}\right) \cdot FU\right) + \left(\left(\frac{b}{a+b}\right) \cdot FU'\right)$$

is greater than zero; and preferably (g) said composition having a glass transition temperature of at least about 150° C., a flex modulus of at least 350 KSI and a fracture toughness of at least 1000 psi √in.

Such polyethers can be prepared by conventional techniques including a process comprising reacting:

(a) a first component selected from the group consisting of bis-phenol compounds of the formula HO—X—OH, where X and Y are defined above with (b) a second component, said second component being a diepoxide selected from the group consisting of is HO—Y—OH, then the diepoxide is chosen from the structure of Formula VII; and (c) a catalytic amount, preferably of 0.1 mole per mole of said first component, of a basic condensation catalyst at a temperature of about 130° to about 230° C. for about 1 to about 24 hours and with a molar ratio of phenol compounds to diepoxides preferably of about 0.90:1 to about 1.04:1 until the desired linear reaction product has been formed, and thereafter stopping the reaction.

A. Bis-phenol Component

In a preferred embodiment the bis-phenol components employed have the structure HO—X—OH or HO—Y—OH where "X" and "Y" are specified above.

When the bis-anthrols and bis-naphthols of Formula Ia and Ib and/or their glycidyl ethers of Formula IIa and IIb are used in the above compositions, the ratio (f) the number of stiff units and flexible units are selected such that the average number of total stiff units $$\left(\left(\frac{a}{a+b}\right) \cdot SU\right) + \left(\left(\frac{b}{a+b}\right) \cdot SU'\right)$$

divided by the average number of total flexible units $$\left(\left(\frac{a}{a+b}\right) \cdot FU\right) + \left(\left(\frac{b}{a+b}\right) \cdot FU'\right)$$

is greater than zero; is preferably from about 1.5 to about 20 and especially from about 2 to about 10.

As a practical matter, it is preferred that the bis-phenol component contain the "X" segment, i.e., that the phenol component be HO—X—OH. The reason for this is that it is usually easier to synthesize the bis-phenol component (containing the relatively large number of stiff units) than it is to glycidate the corresponding diphenol compound. In particular, it is preferred to employ diepoxides based on BPA and use bis-phenol compounds based on the less common compounds. However, in certain cases it may be preferable to have the segment X, in the diepoxide component since the diepoxide may have a lower melting point than the bis-phenol component, resulting in an easier thermoplastic polymer synthesis, especially if it is desired to perform the synthesis in the melt as opposed to a solution preparation.

The stiff units which can be used in the polymers prepared from the bis-anthrols and bis-naphthols or their glycidyl ethers of the invention are selection from the group consisting of substituted or non-substituted aromatic rings, cycloaliphatic rings and heterocyclic

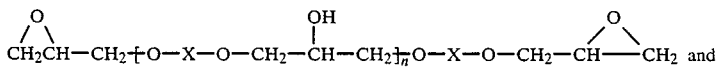

VII.

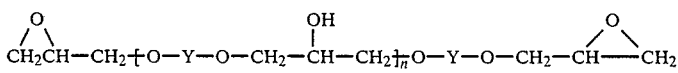

VIII.

wherein if the phenol compound is HO—X—OH, then the diepoxide is chosen from the structure of Formula VII or VIII and if the phenol compound rings. The aromatic rings are inertly substitued or unsubstituted benzene radicals. Substituted benzene radicals have substituents which do not interfere in the process independently selected from the group consisting of Cl, Br or $C_1$-$C_5$ alkyl groups.

A group of bis-phenol compounds are aromatic, cycloaliphatic or heterocyclic rings including those of Formulas Ia and Ib of the invention and those shown below:

(SU = 3, FU = 2)

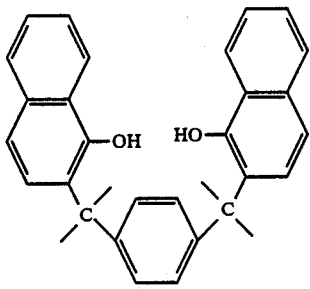

(SU = 5, FU = 2)

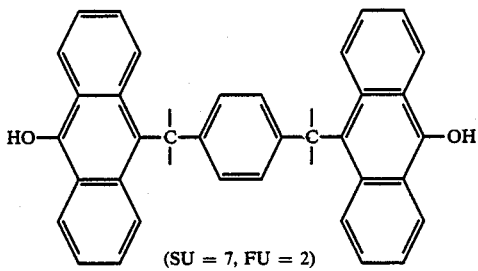

(SU = 7, FU = 2)

This particular illustrated group of bis-phenol compounds are distinguished from bis-phenol compounds such as BPA and the like, by the presence of 2 or more flexible units

and 3 or more stiff units

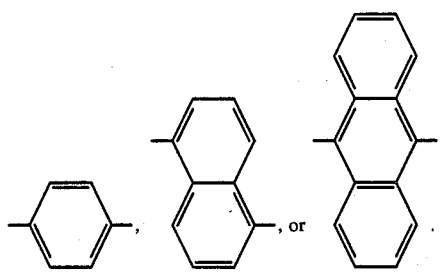

If desired, the bis-phenol compounds described above can be substituted in the polyethers in part (or even in whole in certain cases) with other conventional bisphenols, represented by the formula

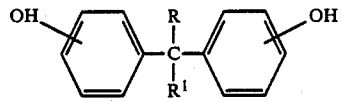

in which R and $R^1$ when taken collectively with the connector carbon C are selected from the group consisting of cyclohexyl and alkyl-substituted cyclohexyl, and when taken separately are from the group consisting of hydrogen, alkyl, cyclohexyl, phenyl, alkyl-substituted cyclohexyl, alkyl substituted phenyl, halogen substituted cyclohexyl and haloen substituted phenyl groups with the total number of carbon atoms in the group or groups attached to said connector carbon atom not exceeding eighteen and the number of carbon atoms in any of said alkyl substituent groups not exceeding six.

B. Diepoxide Component

The second reactant in the condensation process, the diepoxide is a compound having two vicinal expoxide groups (oxirane rings) in terminal (or optionally nonterminal) positions in the molecule, usually in the form of an oxygen atom bound to two terminal carbons of an alkyl group, though the epoxide may also be on a ring, such as a cyclohexyl ring. Suitable diepoxides are terminal diepoxyalkanes, e.g., 1,2-epoxy-3, 4-epoxybutane, 1,2-epoxy-5,6-epoxyhexane, 1,2-epoxy-7,8-epoxyoctane and the like. Others are terminal diepoxides containing ether linkages, such as bis(2,3-epoxypropyl)ether and bis(2,3-epoxy-2-methylpropyl) ether; diglycidyl ethers of alpha,omega glycols such as the diglycidyl ethers of ethylene glycol, trimethylene glycol, and tetramethylene glycol; and diglycidyl ethers of dihydric phenols.

Diglycidyl ethers of the dihydric phenols referred to above are generally suitable for use in this invention. One may suitably use the diglycidyl ether of the same phenol which is employed as the other reactant. Thus, for example, bis-phenol diisopropylbenzene is suitably condensed with diglycidyl ether of alpha, alpha'-bis(1-hydroxy-2-naphthyl)-p-diisopropylbenzene. Useful resins can also be prepared by condensing a dihydric phenol with the diglycidyl ether of a different dihydric phenol. For example, useful condensation products have been prepared according to this invention from the diglycidyl ether of bisphenol A and the dihydric phenol alpha, alpha'-bis(1-hydroxy-2-naphthyl)-p-diisopropylbenzene.

In preparing the products of this invention the epoxy reagent may be a pure diepoxide or a crude mixture containing a substantial proportion of diepoxide, e.g., 70% or more. It is important, however, that the crude reagent is free of monoepoxide and of monohydric alcohol or phenol.

C. Amine Component

The amine component employed in making the polymers of the present invention is selected from the group consisting of primary amines or preferably a bis secondary amine or mixtures thereof.

The primary amines will have the general formula

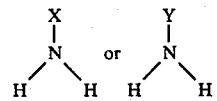

or a mixture thereof where "X" and "Y" are the "X" segments or "Y" segments referred to before.

The bis secondary amines will have the general formula:

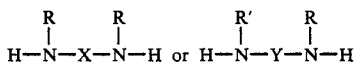

or a mixture thereof where "X" and "Y" segments or "Y" segments referred to before and R and R' are unsubstituted or inertly substituted $C_1$-$C_{20}$ aliphatic, cycloaliphatic or aromatic hydrocarbyl groups. Preferably R and R are $C_1$-$C_{20}$ aliphatic, cycloaliphatic or aromatic hydrocarbyl groups. Preferably R and R' are $C_1$-$C_{20}$ alklyl groups. Examples of R and R' include methyl, ethyl, isopropyl, cyclohexyl, benzyl, tolyl and the like.

Examples of primary monoamines include aniline (phenylamine), 2,6-dimethylaniline, 2,4-dimethylaniline, 2,6-diethylaniline, N-aminophthalimide, 2,6-diisopropylaniline, tolylamine, alpha-naphthylamine, 3-amino-benzothiophene, 1-aminoadamantane, and norbornylamine. Preferred primary monoamines include aniline, 2,6-dimethylaniline and 2,6-diethylaniline with 2,6-diethylaniline being most preferred.

Examples of bis secondary amines include N,N'-dimethyl-p-phenylenediamine, N,N'-dicyclohexyl-p-phenylenediamine, bis(N-sec-butyl-4-aminophenyl)-methane, alpha, alpha'-bis(N-methyl-4-aminophenyl)-p-diisopropylbenzene, alpha, alpha'-bis(N-sec-butyl-4-aminophenyl)-p-diisopropylbenzene, 9,9-bis(N-methyl-4-aminophenyl)-fluorine, N,N'-dimethyl-4,4'-diaminodiphenyl sulfone, and alpha, alpha'-bis(1-amino-2-naphthyl)-para-diisopropylbenzene.

The amine-base resins preferably comprise linear molecules having the repeating structure

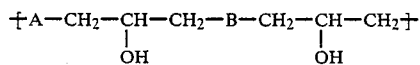

where A is selected from the group consisting of

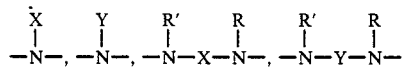

and mixtures thereof and B is selected from the group consisting of

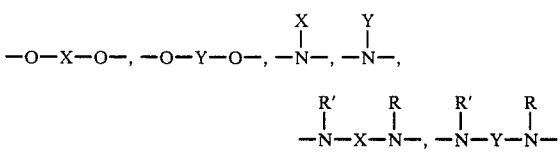

where R and R' are selected from the group consisting of unsubstituted or inertly substituted $C_1$-$C_{20}$ aliphatic, cycloaliphatic or aromatic hydrocarbyl groups, and X and Y are defined above.

Whe preparing copolymers, the reaction is typically carried out in the melt although it is more convenient in solution in a solvent. Desired high impact resistance is a property which can require complete removal of solvent. In the production of resin for use in molding, extrusion, and the like, solvent is removed from the reaction mixture. In the production of resin for surface coatings, the resin may remain associated with solvent until it is actually applied as a coating and the solvent is removed by evaporation under suitable conditions. Its boiling point should be such that the reaction can be carried out at 75° to 150° C. at a practical pressure. The solvent may be a mixture of individual compounds. Useful solvents which meet those criteria are, for example, certain ketones, halogenated hydrocarbons and ethers. Methyl ethyl ketone is a preferred solvent. Cyclohexanone, methyl isobutyl ketone and the other ketones may be used. Chloroform, 1,2-dichloroethane and other chlorinated hydrocarbons may be used, particularly in admixture with ketones. Ethers, such as dioxane, tetrahydrofuran, dimethoxyethane and lower alkyl (methyl or ethyl) ethers of ethylene glycol are suitable, alone or in admixture with ketones. Other solvents which meet the above criteria may be employed if desired, such as N-methyl pyrrolidone.

While in the examples which follow the synthesis was performed in solution, it is possible (and desirable in some cases) to do the synthesis in the absence of solvent, i.e., as a melt. In such cases it may be desirable to use the diepoxide containing the "X" segment since the melting point of diepoxide component is usually much lower than the melting point of the corresponding bis-phenol component.

LIGHT CROSSLINKING

Light crosslinking refers to the crosslinking of between 1 and 50 out of each 100 repeat units to repeat units of other molecules, e.g., Formulas I or II of said thermoplastic polymer. Preferably, the crosslinking density is between 2 and 20 out of 100, more preferably between about 3 and 10 repeat units per 100 units. There are basically three different conventional techniques that can be used to obtain lightly crosslinked matrices: (1) the use of a slightly greater number of diepoxide groups than phenolic or secondary amine groups (see earlier section on Catalyst and Reaction Conditions). When using this technique the repeat units will crosslink through the reaction of the secondary hydroxyl groups with the remaining epoxide groups. Once the thermo plastic polymer is prepared, it may be used alone or with a reinforcing fiber in an FRC-type (fiber reinforced composite) composition, wherein the polymer mass is heated to an elevated temperature (e.g., above 170° C.) and held at that temperature for the necessary time (typically about 2 to about 24 hours) to obtain crosslinking; (2) incorporate an appropriate amount of multifunctional (tri- or higher) epoxide or multifunctional (tri- or higher) phenolic or amine in the preparations of the thermoplastic polymer. The crosslinking agent, when added as a separate component, replaces a portion of the phenolic component or the epoxide component, as desired. For example, if 20% crosslinking agent is used, then 20% of the phenolic or secondary amine component is replaced on an equivalent basis.

Examples of suitable multifunctional epoxide polymers include EPON ® Resin 1031 and EPON Resin DPS-164. EPON Resin DPS-164 has the general formula

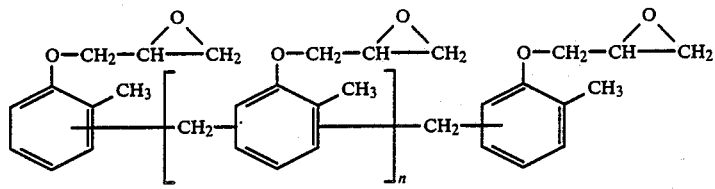

where n equals an average of 3. EPON Resin 1031 has EPON Resin 1031 has the structure

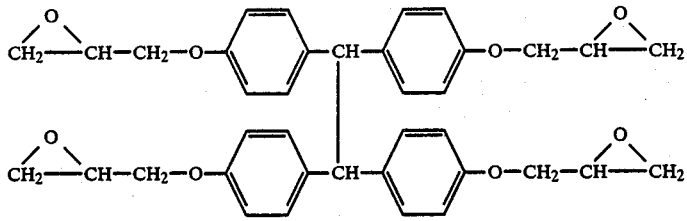

Other crosslinking agents include multifunctional amines such as EPON HPT ™ Curing Agents 1061 and 1062, having the molecular structure:

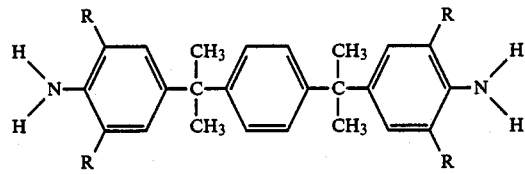

where R is H for CA 1061 and R is CH₃ for CA 1062.
Still other crosslinking agents include

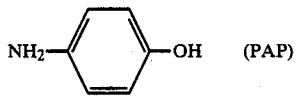

and

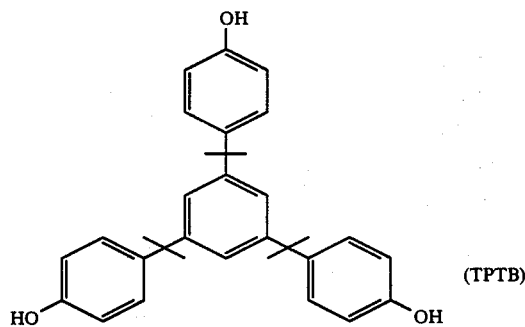

(3) The addition of crosslinking agents, such as triepoxides, etc., to the resulting thermoplastic polymer.

The amount of crosslinking agent chosen is selected to achieve the desired level of light crosslinking, as opposed to the normal crosslinking used for epoxy resins. Accordingly, when using a crosslinking agent such as EPON Resin 1031, the amount of equivalents used is 2 to 20%. Likewise, when the crosslinking agent is EPON HPT Curing Agent 1061, the amount of equivalents used is 5–50%.

While light crosslinked polymers are preferred, full crosslinked or non-crosslinked polymers are within the scope of this invention.

The composition optionally, but preferably for high-performance applications such as automotive and aerospace, contains a reinforcing substrate. Suitable reinforcing materials include, for example, glass fibers, carbon fibers, Kevlar, boron, calcium carbonate, talc, alumina, asbestos and the like. The preferred fibrous reinforcing material for high-performance applications is selected from the group consisting of glass fibers, carbon fibers, boron fibers and Kevlar fibers, with continuous carbon fiber being most preferred. The fibrous reinforcing material will be present in the composition in an amount effective to impart increased strength to the cured composition, generally from about 40 to about 95 weight percent, usually from about 60 to about 80 weight percent, based on the weight of the total composition.

The polyether or polyether amine resin composition can be applied to the fibrous reinforcing material from the melt or solution by methods known in the art. Among the various processes useful with the present invention include resin transfer molding (RTM), pultrusion, filament winding and the use of pre-pregs. Such methods are known in the art, and are disclosed, for example, in the *Handbook of Composites*, Lubin, Ed., Van Nostrand Reinhold Company, 1982, pages 321–532, and in the book by Delmonte titled *Technology of Carbon and Graphite Fiber Composites*, Delmonte, Van Nostrand Reinhold Company, 1981.

On method of current preferred interest involves the use of pre-pregs. In that system, the polymer composition/curing agent-impregnated substrate, or "pre-preg", or a laminate prepared from a plurality of pre-pregs, is then cured. When the system is based on a polyether of the diglycidyl ether of alpha, alpha'-bis(1-hydroxy-2-naphthyl)-p-diisopropylbenzene and bisphenol diisopropylbenzene, the curing is typically accomplished at a temperature of about 150° to about 200° C. for about 1 to about 16 hours under vacuum or under a presence of 1 atmosphere to 150 psi, to form the structural composite article.

The polyether resin compositions have particular application in the aerospace industry where the high performance obtainable with the present invention is required. In particular, RTM may be used to prepare large parts, such as helicopter blades. Pre-pregs may be used tu prepare parts such as wings and the like. Filament winding may be used to prepare an entire fuselage, while pultrusion may be used to prepare parts having a constant cross section. The composition can optionally include additives for control or modification of various properties of the composition in its cured or uncured state, including cure rate accelerators or retardants, tackifiers and the like.

ILLUSTRATIVE EMBODIMENTS

To illustrate the present invention, the following illustrative embodiments are given. It is to be understood, however, that the embodiments and examples are given for the purpose of illustration only and the invention is not to be regarded as limited to any of the specific materials or conditions used in the specific embodiments.

Embodiment 1-α,α'-bis(10-anthr-9-one)-p-diisopropylbenzene (BADB)

BADB was synthesized by charging a stirred reactor with anthrone, p-diol [bis-p-(1-hydroxy-1-methylethyl)-benzene] and 1,1,2-trichloroethane in a molar ratio of 4:1:7 and heating to 100° C. under nitrogen and reflux condenser. Concentrated aqueous HCl (1.02 moles as 100% HCl/mole p-diol) was charged at 100° C. with an addition funnel. BADB was recovered by filtration and purified by washing with methanl, slurrying in boiling toluene, filtering and washing with methanol again. The yield was about 60% of fine yellow crystals with melting point-255°-265° C. The chemical structure of BADB was confirmed by C13 solid state NMR.

Embodiment 2-Diglycidyl α,α'-bis(10-anthr-9-one)-p-diisopropylbenzene (DGBADB)

DGBADB was synthesized by charging a stirred reactor with BADB of Embodiment 1, potassium t-butoxide (KTBA), and toluene in a molar ratio of 1:2.4:65 and heating to 110° C. for 1 hour under nitrogen. T-butanol was continuously removed as the toluene azeotrope and fresh toluene added back to the reactor. The reaction mass remained a slurry throughout this step, but the color changed from yellow to crimson red as the potassium salt of BADB was formed. After 1 hour at 110° C., the red slurry was cooled to 40° C. Epichlorohydrin (20-200 moles/mole BADB) was charged all at once with an addition funnel and the mass was reacted 60-90 minutes at 70° C. During this step the red BADB salt went into solution and crystals of KCl and uncovered BADB crystallize out. The crude product was recovered by first cooling the reaction mass and allowing the solids to settle. The supernatent was decanted through a filter and the product recovered by vacuum evaporating at 100° C. maximum (no longer than 10 minutes at this temperature) under 1-5 mm Hg vacuum. The crude product was dissolved 20% wt. in methylisobutyl ketone (MIBK) and water washed until the wash water was neutral. The final product was recovered by vacuum evaporating the MIBK. The DGBADB obtained had a weight per epoxy equivalent (WPE)=395-450 (theoretical WPE=331), sponifiable chlorine (Sap Cl)=0.01% wt., and melting point=160°-170° C. The chemical structure of DGBADB was supported by C13 solution NMR end group analysis experiments.

Embodiment 3-9,9-bis(1-hydroxy-2-naphthyl)-fluorene (BNFL)

BNFL was synthesized by charging 1-naphthyl, 9-fluorenone, 1,1,1-trichloroethane, p-toluenesulfonic acid, and 3-mercaptopropionic acid to a stirred reactor in a molar ratio of 8:1:4:0.5:0.1 and heated to 90° C. for 2 hours under nitrogen and reflux condenser. After 5 minutes at 90° C. crystals formed in the reaction mass. When the reaction mass went solid with crystals, more 1,1,1-trichloroethane was added and the reaction was continued. The reaction mass was cooled by the addition of a portion of isopropyl alcohol (IPA) and the product removed by filtration and washed with IPA. BNFL was obtained in 91% yield as white crystals with melting point=268°-290° C. The chemical structure for BNFL was supported by C13 and Proton solution NMR.

Embodiment 4-α,α'-bis(1-hydroxy-2-naphthyl)-p-diisopropylbenzene (BNDB)

BNDB was synthesized by charging 1-naphthol, p-diol as [bis-p-(1-hydroxy-1-methylethyl)benzene], and 1,1,2- or 1,1,1-trichloroethane to a stirred reactor in a molar ratio of 8:1:4 and heating to 70° C. under nitrogen and a reflux condenser. Concentrated aqueous HCl (1.02 moles as 100% HCl:mole p-diol) was charged at 70° C. with an addition funnel. The reaction mass was heated at 80° C. for 1 hour after the addition of the HCl was complete. BNDB began crystallizing out of the reaction mass 10-15 minutes after the first HCl was added. At the end of 1 hour, the reactor was thick with BNDB crystals. IPA was added as the slurry was cooled to aid in filtration of the BNDB. BNDB was collected by filtration and washed several times (until white) with IPA. The filtrate was slurried in boiling IPA and collected by filtration again. The white crystalline BNDB (90-95% yield), melting point=245°-255° C., was of suitable purity for making the epoxy resin. BNDB was also recrystallized out of tetrahydrofuran (14% wt. BNDB). The chemical structure of BNDB was confirmed by C13 and Proton solution NMR, X-ray Diffraction and Mid-Infra Red experiments.

Embodiment 5-Diglycidyl of α,α'-bis(1-hydroxy-2-naphthyl)-p-diisopropylbenzene (DGBNDB)

DGBNDB is made by charging BNDB, epichlorohydrin (ECH), iospropanol (IPA), and water to a stirred reactor in a molar ratio of 1.0:15.0:13.5:12.0 and heating to 70° C. under nitrogen and a reflux condenser. At 70° C. the reaction mass was a slurry. 20% wt. sodium hydroxide (3.0 moles sodium hydroxide per mole of BNDB) was added to the hot reaction mass in stages over 80 minutes. BNDB had reacted into solution by the end of the first NaOH addition period. The organic phase was washed with hot-deionized water until the wash water was neutral. As the organic phase cooled and became more concentrated, DGBNDB had a tendency to crystallize out of solution. The DGBNDB containing organic phase was vacuum evaporated to give the desired product with a WPE=316, Sap Cl=0.04-0.06% wt. The product was dissolved in methyl-isobutyl ketone (MIBK), 20-30% wt. resin, and doing a second dehydrohalogenation reaction using 5% wt. aqueous NaOH. The resin solution was heated 2 hours at reflux under nitrogen with 20–25% wt. (based on the wt. of the resin solution) of 5% wt. aqueous NaOH. The brine was removed and the resin solution washed with hot de-ionized water until the wash water was neutral. The hot resin solution was filtered to remove any insoluble material, and then concentrated by distillation to approximately 50% wt. resin. DGBNDB crystallized out as the solution cooled and was collected by filtration. The white crystalline DGBNDB had a WPE=281 (theoretical WPE=279), Sap cl= <0.01% wt., and melting point=167°–168° C. The chemical structure of DGBNDB was confirmed by C13 and Proton solution NMR.

Embodiment 6

A variety of phenolic and amine curing agents was used to polymerize the diglycidyl ethers of the invention as follows:

DGBNDB/amine polymers were made by dissolving the monomers in a vacuum erlenmyer flask at 190° C. at the desired stoichiometry and treating with the curing agent. Mixing was facilitated by pulling pump vacuum (1–5 mm Hg vacuum) on the erlenmyer and degassing while dissolution occurred. In the case of DGBNDB-based polymers made by a phenolic cure, MBTPP (methylene-bis-triphenylphosphine dibromide; 0.0024 equivalents Br/equivalent epoxy) was added after the monomers were dissolved and homogeneous. The polymers (unless otherwise noted) were cured at 190° C. for 24 hours in a forced draft oven.

The prepolymer mixtures were poured between preheated glass plates which had been pretreated with Surfasil TM Siliconizing Agent (Pierce Chemical Company). The glass plates were separated by ⅛ in. teflon bead in a horseshoe shape and were clamped together. Typical casting size for a full spectrum of mechanical testing was 40 grams. The resulting compositions are set forth in the table below.

| Diglycidyl Ether | Curing Agent or Co-monomer | Ratio of Phenol (P) or Amine (NH) to Epoxide (E) |
|---|---|---|
| DGBNDB | NMADB | NH/E = 1.0 |
| DGBNDB | NMADB 13% ADB | NH/E = 1.0 |
| DGBNDB | NMADB 26% ADB | NH/E = 1.0 |
| DGBNDB | NMADB 50% ADB | NH/E = 1.0 |
| DGBNDB | NMADB 75% ADB | NH/E = 1.0 |
| DGBNDB | ADB | NH/E = 1.0 |
| DGBNDB | BPDB 15% TPTB | P/E = 1.0 |
| DGBNDB | BPDB 25% TPTB | P/E = 1.0 |
| DGBNDB | BPDB 35% TPTB | P/E = 1.0 |
| DGBNDB | BPDB 50% TPTB | P/E = 1.0 |
| DGBNDB | BPDB 75% TPTB | P/E = 1.0 |
| DGBNDB | BPDB | P/E = 0.96 |
| DGBNDB | BPA | P/E = 0.96 |
| DGBNDB | DMA 15% DMADB | NH/E = 1.0 |
| DGBNDB | THQ 15% ADB | NH/E = 1.0 |
| DGBNDB | NBMDA 25% MDA | NH/E = 1.0 |
| DGBNDB | NBMDA | NH/E = 1.0 |

| Diglycidyl Ether | Curing Agent or Co-monomer | Ratio of Phenol (P) or Amine (NH) to Epoxide (E) |
|---|---|---|
| | 50% MDA | |

DGBNDB Diglycidyl ether of alpha, alpha'-bis(1-hydroxy-2-napthyl)-p-diisopropylbenzene
NMADB alpha, alpha'-bis(N—methyl-4-aminophenyl)-p-diisopropylbenzene
ADB alpha, alpha'-bis(4-aminophenyl)-p-diisopropylbenzene (EPON Curing Agent HPT 1061)
BPDB alpha, alpha'-bis(4-hydroxyphenyl)-p-diisopropylbenzene
TPTB alpha, alpha', alpha''-tris(4-hydroxyphenyl)-1,3,5-triisopropylbenzene
BPA 2,2-bis(4-hydroxyphenyl)propane
DMA 2,6-dimethylaniline
DMADB alpha, alpha'-bis(4-amino-3,5-dimethylphenyl)-p-dissopropylbenzene (EPON Curing Agent HPT 1062)
NBMDA N,N$^1$—di-sec-butyl methylene dianiline
THQ 1,2,3,4-tetrahydroquinoxaline The polymer compositions were tested according to the following test procedures:

Flexural properties of neat resins were evaluated according to ASTM D790 method using ⅛ in. thick specimens. Specimens were tested both in Dry (at Room Temperature and ~75% R.H.) and Hot/Wet (after immersion in boiling water for 48 hours, test at 200° F., 5 min. equilibration time) conditions.

Fracture toughness, $K_q$, was measured using mini-compact tension specimens (see W. B. Jones, et. a. Am. Chem. Soc. Soc., Div. Polym. Chem., Polym. Prepr., 22, 1981). All specimens were slotted to a Chevron shape and then precracked with a razor blade.

Tensile properties were measured according to ASTM D638 method.

Swelling in solvents was evaluated by measuring weight gain per unit of initial weight after immersion in solvent for a specified time at room temperature.

The resulting polyether thermoplastic compositions had the characteristics of a thermosetting polymer along with an improved balance of properties including solvent resistance and improved modules/glass transition temperature/toughness balance as determined by the test procedures set forth above.

What is claimed is:

1. A bis-anthrol or a bis-naphthol of the formula Ia or Ib or the keto tautomer of Ia

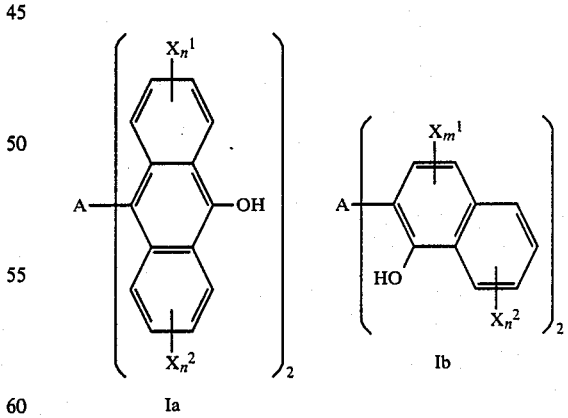

Ia            Ib wherein $X^1$ and $X^2$ each independently is an alkyl group containing from 1 to 4 carbon atoms or a halogen atom having an atomic number of from 9 to 35, inclusive; m is 0, 1 or 2; n is 0, 1, 2, 3 or 4; and A is a divalent dialkyl aromatic or dialkyl non-aromatic carbocyclic group containing from 7 to 24 carbon atoms in which each alkyl group contains from 1 to 8 carbon atoms and in which the carbocyclic comprises (1) a central non-aromatic carbocyclic ring containing 5 to 7 carbon atoms in a ring, or (2) a central aromatic carbocyclic ring, wherein the central ring of (1) or (2) may be bridged or fused with one or two non-aromatic or aromatic carbocyclic rings; and wherein the anthrol or naphthol group is directly attached to alkyl substituents of the dialkyl carbocyclic group.

2. A bis-anthrol or a bis-naphthol according to claim 1 wherein $X^1$ and $X^2$ are each independently methyl groups or chlorine atoms.

3. A bis-anthrol or a bis-naphthol according to claim 2 wherein m and n are 0.

4. A bis-anthrol or a bis-naphthol according to claim 3 wherein A is a phenylene-p-diisopropylidene group or a naphthylenediisopropylidene group.

5. A bis-naphthol according to claim 4 wherein A is a phenylene-p-diisopropylidene group.

6. A bis-naphthol according to claim 4, wherein A is a naphthylene-diisopropylidene group.

7. 9,9-bis(1-hydroxy-2-naphthyl)fluorene.

* * * * *